United States Patent [19]

Chan

[11] 4,253,865
[45] Mar. 3, 1981

[54] 1,1-DIOXO-2-HALOHYDROCARBYLTHIO-1,2-BENZOISOTHIAZOLIDINES

[75] Inventor: David C. K. Chan, Petaluma, Calif.

[73] Assignee: Chevron Research Company, San Francisco, Calif.

[21] Appl. No.: 72,872

[22] Filed: Sep. 6, 1979

[51] Int. Cl.³ .................. A01N 43/80; C07D 275/06
[52] U.S. Cl. ........................................ 71/91; 548/207
[58] Field of Search ............................ 548/207; 71/91

[56] References Cited

U.S. PATENT DOCUMENTS

| | | | |
|---|---|---|---|
| 3,164,602 | 1/1965 | Childress et al. | 548/207 |
| 3,166,563 | 1/1965 | Epstein et al. | 548/207 |
| 3,303,190 | 2/1967 | Loev | 544/49 |
| 3,673,200 | 6/1972 | Baker et al. | 71/91 |
| 4,108,627 | 8/1978 | Bollenger et al. | 71/91 |

FOREIGN PATENT DOCUMENTS 2105580  9/1972  Fed. Rep. of Germany ........... 548/207

OTHER PUBLICATIONS

Cheyomaru et al.; Chem. Abs., vol 77: 164667p, (1972).
Staehle et al.; Chem. Abs., vol.77: 164669r, (1972).
Ponci et al.; Chem. Abs., vol 66: 37816j, (1967).
Levy; Chem. Abs., vol. 76: 14414u, (1972).
Renfrow; J. Org. Chem., vol. 40, pp. 1525–1526, (1975).
Levy; J. Het. Chem., vol. 8, pp. 873–874, (1971).

*Primary Examiner*—Mary C. Lee
*Attorney, Agent, or Firm*—D. A. Newell; T. G. DeJonghe; R. J. Suyat

[57] ABSTRACT

Compounds of the formula:

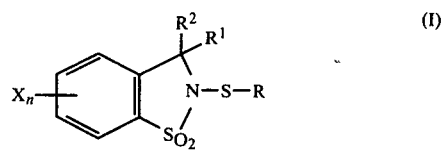

wherein R is haloalkyl, haloalkenyl or halogenated aryl; $R^1$ and $R^2$ are hydrogen, alkyl or are joined to form a cyclopentyl or cyclohexyl ring; X is hydrogen, halo, alkyl, haloalkyl, alkoxy, nitro or cyano; and n=1 to 5 have fungicidal and bactericidal activity.

8 Claims, No Drawings

1,1-DIOXO-2-HALOHYDROCARBYLTHIO-1,2-BENZOISOTHIAZOLIDINES

BACKGROUND OF THE INVENTION

U.S. Pat. Nos. 3,303,190 and 3,303,191 disclose dihydro-2,1-benzothioazine-2,2,-dioxides and 4-ketodihydro-2,1-benzothiazine 2,2-dioxides, respectively, having pharmaceutical utility.

Levy discloses the synthesis of N-methoxy benzisothiazoles in *J. Heterocycl. Chem.*, 8, 873 (1971).

Renfrow et al. disclose benzylsultam as a product of gas-phase thermolysis of 2-methylbenzenesulfonyl azide in *J. Org. Chem.*, 40, 1525–6 (1975).

Phaltan (N-trichloromethylthio-phthalimide), Difolatan ® (cis-N-(1,1,2,2-tetrachloroethylthio)-4-cyclohexene-1,2-dicarboximide) and Captan (N-(trichloromethylthio)-4-cyclohexene-1,2-dicarboximide) are known fungicides.

SUMMARY OF THE INVENTION

The present invention relates to novel fungicidal and bactericidal compounds, compositions thereof and methods of their use. The compounds of the invention are particularly effective against *Xanthomonas vesicatoria, Phytophthora infestans, Rhizoctonia solani, Fusarium moniloforma* and *Botyrtis cinera*. Among other factors, my invention is based on my finding that while S-dioxobenzthiazolidines are not known to have fungicidal or bactericidal activity useful on plants, I have found that 1,1-dioxo-2-halohydrocarbylthio-1,2-benzisothiazolidines do have such activity.

DESCRIPTION OF THE INVENTION

This invention relates to compounds represented by the formula

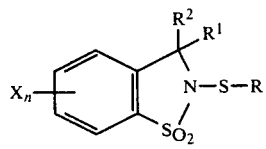

where R is haloalkyl of 1 to 5 carbon atoms and 1 to 10 halogen atoms, haloalkenyl of 2 to 6 carbon atoms and 1 to 10 halogen atoms or halogenated aryl of 6 to 10 carbon atoms and 1 to 6 halogen atoms;

$R^1$ and $R^2$ are independently hydrogen, alkyl of 1 to 6 carbon atoms or $R^1$ and $R^2$ are joined to form a 5 or 6-membered aliphatic ring;

X is hydrogen, halogen, alkyl of 1 to 4 carbon atoms, haloalkyl of 1 to 4 carbon atoms and 1 to 9 halogen atoms, alkoxy of 1 to 4 carbon atoms, nitro or cyano; and n=1 to 5.

Representative $R^1$ and $R^2$ group are hydrogen, methyl, ethyl, n-propyl, i-propyl, etc. Preferably $R^1$ and $R^2$ are hydrogen.

Representative X groups are hydrogen, chloro, bromo, fluoro, methyl, ethyl, i-propyl, trifluoromethyl, 1,1,2,2-tetrachloroethyl, methoxy, ethoxy, nitro and cyano. Preferably X is hydrogen and n=4.

Representative R groups are chloromethyl, dichloromethyl, 1,1,2,2-tetrachloroethyl, 1,2,2,2-tetrachloroethyl, chlorofluoromethyl, trichlorovinyl and B 2,4-dichlorophenyl. Preferably R is 1,1,2,2-tetrachloroethyl.

The compound of the invention may be made by the following scheme:

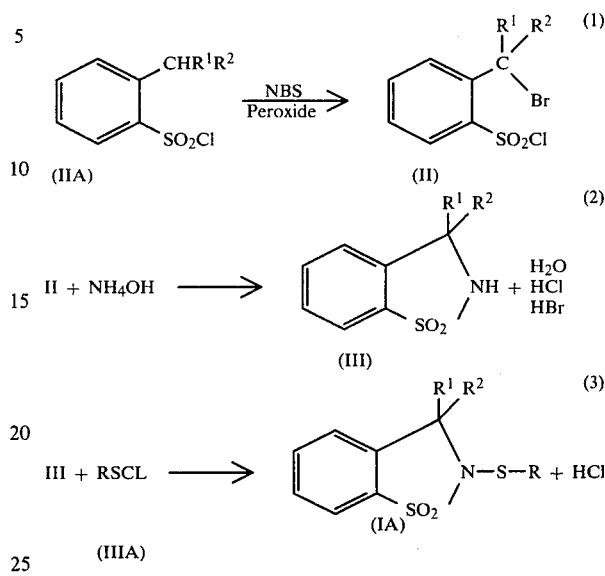

Reaction (1) may be conducted by reacting a substantially equimolar amount of the sulfonyl chloride (IIA) with N-bromosuccinimide in the presence of a peroxide initiator, such as, benzoyl peroxide, in an inert solvent, such as, carbon tetrachloride, at reflux temperature.

Reaction (2) may be conducted by reacting the bromoalkyl compound (II) with ammonium hydroxide in the presence of a strong base, preferably, sodium hydroxide, at from about $-15°$ C. to $0°$ C. in an inert solvent according to the procedure of Renfrow et al.

Reaction (3) may be conducted by reacting substantially equimolar amounts of the benzisothiazolidine (III) and the alkylthiochloride (IIIA) in the presence of a strong base, such as, sodium hydroxide, and a catalytic amount of benzyl triethyl ammonium chlorid in an inert solvent at room temperature.

The compounds of the invention have been found useful for controlling bacteria, algae and fungi, particularly plant infections caused by organisms such as *Phytophthora infestans, Septoria apii, Rhizoctonia solani, Fusarium moniloforma, Botrytis cinerea, Aspergillus niger,* and *Xanthomonas vesicatoria.*

When used as fungicides, the compounds of the invention are applied in fungicidally effective amounts to fungi and/or their habitats, such as vegetative hosts and non-vegetative hosts, e.g. animal products. The amount used will, of course, depend on several factors such as the host, the type of fungus and the particular compound of the invention. As will most pesticidal compounds, the fungicides of the invention are not usually applied full strength, but are generally incorporated with conventional biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5–80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comporises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant. Useful liquid concentrates include the emulsifiable concentrates which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, iosphorone, and other nonvolatile organic solvents. For application, these concentrates are dispsersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant growth regulators, fertilizers, etc.

When used as bactericides, the compounds of this invention are formulated and applied in bactericidal amounts by conventional art methods to bacteria or hosts (growth environment) which are subject to bacterial attack, especially vegetative hosts such as plants, plant seeds, etc. The amount used will, of course, depend on several factors such as the host, the type of bacteria, and the particular activity of the compound used. The compounds of this invention may be combined with inert liquids and solid carriers such as powders, solutions, dispersions, etc., for such use. The compounds of this invention will generally be admixed with biologically inert liquids or solids in an amount from about 0.05 to 95 weight percent. Higher or lower amounts, of course, can be used. Preferably from 1 to 50 weight percent of the composition will be the active compound of the present invention.

Typical solid carriers which are suitably used to formulate the compounds are clay, talc, chalk and sawdust. Representative solvents which are suitably used to formulate the compounds include aromatic hydrocarbons such as xylene, benzene, toluene, petroleum fractions, alcohols (especially low molecular weight alkanols) and chlorinated aliphatic hydrocarbons such as chloroform, methylene chloride and the like. These formulations may also contain emulsifying agents, sticking agents, fillers and other compatible pesticides.

EXAMPLE 1

Preparation of 1,1,-Dioxo-2-(1,1,2,2-tetrachloroethylthio)-1,2-benzoisothiazolidine A mixture of 2-methylphenylsulfonyl chloride (97.5 g), N-bromo succinimide (89.0 g) and benzoyl peroxide (5 g) in 550 ml carbon tetrachloride was refluxed for 3 hours. The solution was filtered and the liquor was stripped. The residue was micro-distilled. 2-Bromomethylphenyl sulfonyl chloride (A) was collected at 112°–113° C. at 0.1–0.18 mm Hg.

A solution of 40 ml 2.5 N sodium hydroxide, 11 ml ammonium hydroxide and 360 ml diethyl ether was cooled to about $-10°$ C. A solution of 11.6 g of A in 380 ml diethyl ether was added with vigorous stirring. After stirring for 15 minutes the solution was stripped, diluted with water (100 ml), and extracted (first extract) with dichloromethane. The aqueous phase was acidified (10% HCl) and extracted (second extract, $2\times50$ ml) with dichloromethane. The second extract was dried ($MgSO_4$), filtered and stripped (Yield 1.3 g 1,1-dioxo-1,2-benzoisothiazolidine (B)). The first extract was acidifed, washed ($H_2O$), dried ($MgSO_4$), filtered and stripped. The residue was washed with ether to yield an additional 2.8 g of B.

A mixture of B (4.1 g), 1,1,2,2-tetrachloroethyl sulfenyl chloride (5.7 g) and benzyl triethyl ammonium chloride (1 g) in 100 ml dichloromethane was stirred at ice bath temperature with addition dropwise of a 50% aqueous solution of sodium hydroxide (1.9 g NaOH in $H_2O$). The mixture was stirred at room temperature for one hour.

The solution was washed ($3\times100$) with water, dried ($MgSO_4$), filtered, and stripped under reduced pressure. The solid product was washed with cold acetone to yield the title product, m.p. 172°–175° C.

Analysis: S Calc: 17.47 Fd: 17.8. Cl Calc: 38.63 Fd: 37.5.

EXAMPLE 2

Tomato Late Blight

The compound of Example 1 was tested for the control of the Tomato Late Blight organism *Phytophthora infestans conidia*. Six- to seven-week-old tomato (variety Bonny Best) seedlings were used. The tomato plants were sprayed with a 250-ppm solution of the test compound in acetone, water and a small amount of a nonionic emulsifier. the sprayed plants were then inoculated one day later with the organism, placed in an environmental chamber and incubated at 19°-20° C. and 100% relative humidity for at least 16 hours. Following the incubation, the plants were allowed to dry and then were maintained at 60-80% relative humidity for approximately 7 days. The percent disease control provided by the test compound based on the percent disease reduction relative to untreated check plants was 99%.

EXAMPLE 3

Celery Late Blight

The compound of Example 1 was tested for the control of Celery Late Blight using celery (Utah) plants 12 to 14 weeks old. The Celery Late Blight organism was *Septoria apii*. the celery plants were sprayed with 250 ppm solutions of the test toxicant mixed with acetone, water and a nonionic emulsifier. The plants were then inoculated with the organism and placed in an environmental chamber and incubated at 19°-20° C. in 100% relative humidity for an extended period of time (approximately 48 hours). Following the incubation, the plants were allowed to dry and then were maintained at a 60-80% relative humidity for approximately 14 days. The percent disease control provided by the test compound based on the percent disease reduction relative to untreated check plants was 77%.

EXAMPLE 4

Bactericide Test

This method is designed to test the compound of Example 1 against *Xanthomonas vesicatoria* on tomato under greenhouse conditions. The plants were sprayed with a 500 ppm solution of the test toxicant in acetone and water and a small amount of nonionic surfactant. The treated plants were allowed to dry and then inoculated with the bacteria. The inoculated plants were transferred to semi-controlled greenhouses maintained at 60-80% relative humidity. The rate of disease development was determined after a period of time for each bacteria. The percent control baeed on a bacterial count on toxicant treated plants compared with nontreated control plants was 100%.

EXAMPLE 5

Mycelial Inhibition

The compound of Example 1 was evaluated for fungicidal effectiveness by means of a mycelial inhibition test. This test is designed to measure the fungitoxic activity of fungicidal chemicals in terms of their degree of inhibition of mycelium growth. Each compound to be tested was dissolved in acetone to 500 ppm concentration. Paper strips were inoculated with the particular mycelium growth by covering the paper with a potato dextrose broth culture or mycelial suspension. The inoculated papers were then placed on potato extrose agar plates and sprayed by means of a micro sprayer with the fungicidal solution. The treated paper strips were incubated at 25° C. and data is taken after 24 hours. Fungicidal activites are measured by a zone of inhibited mycelial growth from the center of the paper strip. The effectiveness of the compound tested for fungicidal activity is measured in terms of the microgram/cm² for 99% control of the fungus (the $ED_{99}$ value). The effectiveness is reported below in terms of the percentage of the test $ED_{99}$ value of the standard $ED_{99}$ value. Phaltan is the standard for Botrytis and DIfolatan ® is the standard for all others.

| | |
|---|---|
| *Rhizoctonia solani* | 100 |
| *Fusarium moniloforma* | 200 |
| *Botrytis cinerea* | 100 |
| *Aspergillus niger* | 111 |

What is claimed:

1. A compound of the formula:

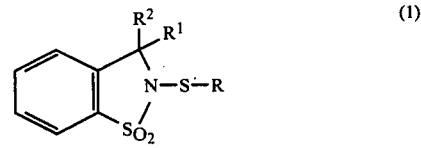

(1)

wherein R is haloalkyl of 1 to 5 carbon atoms and 1 to 10 halogen atoms, haloalkenyl of 2 to 6 carbon atoms and 1 to 10 halogen atoms or halogenated aryl of 6 to 10 carbon atoms and 1 to 6 halogen atoms; $R^1$ and $R^2$ are independently hydrogen, alkyl of 1 to 6 carbon atoms or $R^1$ and $R^2$ are joined to form a 5- or 6-membered aliphatic ring.

2. A compound according to claim 1, wherein $R^1$ and $R^2$ are hydrogen.

3. A compound according to claim 2, wherein R is haloalkyl of 1 to 5 carbon atoms and 1 to 10 halogen atoms.

4. A compound according to claim 3, wherein R is 1,1,2,2-tetrachloroethyl.

5. A fungicidal composition comprising a fungicidally effective amount of a compound defined in claim 1 and a biologically inert carrier.

6. A method for the control of fungi which comprises contacting said fungi or their habitats with a fungicidally effective amount of a compound defined in claim 1.

7. A bactericidal composition comprising a bactericidally effective amount of a compound defined in claim 1 and a biologically inert carrier.

8. A method for the control of bacteria which comprises contacting said bacteria or their habitats with a bactericidally effective amount of a compound defined in claim 1.

* * * * *